US008012171B2

(12) United States Patent
Schmieding

(10) Patent No.: US 8,012,171 B2
(45) Date of Patent: *Sep. 6, 2011

(54) HIGH STRENGTH SUTURE WITH PBO

(75) Inventor: John Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1319 days.

This patent is subject to a terminal disclaimer.

(21) Appl. No.: 11/349,280

(22) Filed: Feb. 8, 2006

(65) Prior Publication Data

US 2006/0178701 A1 Aug. 10, 2006

Related U.S. Application Data

(60) Provisional application No. 60/650,984, filed on Feb. 9, 2005.

(51) Int. Cl.
*A61B 17/04* (2006.01)
(52) U.S. Cl. ........................................ 606/228; 606/230
(58) Field of Classification Search .................. 606/228, 606/229, 230, 231
See application file for complete search history.

(56) References Cited

U.S. PATENT DOCUMENTS

| 6,045,571 | A | 4/2000 | Hill et al. |
| 6,716,234 | B2 * | 4/2004 | Grafton et al. ................ 606/228 |
| 6,994,719 | B2 * | 2/2006 | Grafton ......................... 606/228 |
| 7,029,490 | B2 * | 4/2006 | Grafton et al. ................ 606/228 |
| 7,168,231 | B1 * | 1/2007 | Chou et al. ....................... 57/210 |
| 2003/0008584 | A1 | 1/2003 | Thomas |
| 2003/0050667 | A1 * | 3/2003 | Grafton et al. ................ 606/228 |
| 2003/0079732 | A1 | 5/2003 | Simonds |

FOREIGN PATENT DOCUMENTS

EP   1 293 218   3/2003

* cited by examiner

*Primary Examiner* — Darwin Erezo
*Assistant Examiner* — Steven Ou
(74) *Attorney, Agent, or Firm* — Dickstein Shapiro LLP

(57) ABSTRACT

A high strength abrasion resistant surgical suture material with improved tie down characteristics and tissue compliance includes poly(p-phenylene-2,6-benzobisoxazole) (PBO). The suture features a multifilament jacket formed of braided strands of PBO, optionally with fibers of polyester, silk, nylon or aramid strands as an enhancer. In one embodiment, the braided jacket surrounds a core formed of twisted strands of PBO. The suture has exceptional strength, is ideally suited for most orthopedic procedures, and can be attached to a suture anchor or a curved needle.

17 Claims, 3 Drawing Sheets

HIGH STRENGTH SUTURE WITH PBO

CROSS-REFERENCE TO RELATED APPLICATIONS

This application claims the benefit of U.S. Provisional Application Ser. No. 60/650,984, filed on Feb. 9, 2005, the disclosure of which is incorporated by reference herein. The present application is also related to the following U.S. patent application Ser. No. 10/970,381, filed Oct. 22, 2004, U.S. application Ser. No. 10/358,399, filed Feb. 5, 2003, now U.S. Pat. No. 6,994,719, which is a continuation-in-part of U.S. application Ser. No. 10/160,176, filed Jun. 4, 2002, now U.S. Pat. No. 7,029,490, which claims the benefit of U.S. Provisional Application No. 60/354,499, filed Feb. 8, 2002, U.S. Provisional Application No. 60/350,040, filed Jan. 23, 2002, and U.S. Provisional Application No. 60/330,913, filed Nov. 2, 2001, which is a continuation-in-part of U.S. application Ser. No. 09/950,598, filed Sep. 13, 2001, now U.S. Pat. No. 6,716,234.

BACKGROUND OF THE INVENTION

1. Field of the Invention

The present invention relates to high strength surgical suture materials, and more particularly to braided surgical suture including high performance fibers based on rigid-rod molecules of poly(p-phenylene-2,6-benzobisoxazole) (PBO). PBO is sold under the registered trademark Zylon® by Toyobo Co. Ltd.; http://www.toyobo.co.jp; 2-8, Dojima Hama 2-chome, Kita-ku, Osaka, 530-8230, Japan. PBO is also sometimes referred to in the literature as poly-p-phenylenebenzobisoxazole, and the two are used interchangeably herein.

2. Description of the Related Art

Suture strength is an important consideration in any surgical suture material. Strong fiber materials currently formed into elongated strands include PBO. PBO has been woven into materials used to produce body armor, for example. Fibers of this material are much stronger than those used to make ordinary surgical suture.

High strength sutures formed with materials incorporating PBO would add to the surgical arts, particularly in areas of orthopedic surgery. Most beneficial would be high strength sutures with PBO that manifest acceptable knot tie-down characteristics and handling.

SUMMARY OF THE INVENTION

The present invention advantageously provides a high strength suture material with surgically-useful qualities, including knot tie down characteristics and handling. The suture features PBO fibers (strands made in whole or in part of PBO filaments), optionally blended with enhancement strands to improve handling characteristics and tissue compatibility, for example, of the high strength suture material. Enhancements in tissue compatibility include improving compliance by allowing the ends of the suture to be cut close to the knot without concern for deleterious interaction between the ends of the suture and surrounding tissue. Other enhancements include incorporating visible traces into the finished suture.

The high strength sutures of the present invention preferably are formed by braiding. Plain hollow braids of PBO are most preferred, though the various other types of braiding can be used. One or more enhancement fibers can be blended into the braid. The sutures also can include a core, preferably formed of twisted fibers. In an exemplary embodiment, the core includes, or is made exclusively of, PBO. Other core fibers can be used in place of or in addition to PBO.

As a further enhancement, strands of a contrasting color added to the braided threads make the suture more discernable during surgical procedures. The colored strands preferably are dyed filaments or strands. Natural fibers, such as silk, and some synthetic fibers, accept dye more readily than others. Other synthetic fibers can be colored during manufacture by tinting the polymeric material from which they are formed. In a further aspect of the invention, colored traces can be produced by exposing the braided suture material to a dye that is accepted by some strand materials and rejected by others. Those strands that accept the dye become the colored trace, while strands that reject the dye remain their original color, such as translucent or white. In one embodiment, half of a length of suture is provided with tinted tracing strands, or otherwise contrasts visually with the other half of the length of suture, which remains a plain, solid color, or displays a different tracing pattern, for example. Accordingly, when the length of suture is loaded through the eyelet of a suture anchor or passed through tissue, for example, at least one of the legs of the suture is visually coded, making identification and handling of the suture legs simpler. Easy identification of suture in situ is advantageous in surgical procedures, particularly during arthroscopic surgeries and others, such as endoscopy and laparoscopy, that currently are generally referred to as "minimally invasive."

In a preferred embodiment, the suture includes a multifilament jacket or sheath formed of braided PBO. Optionally, the PBO can be braided with an enhancement fiber from the group consisting of polyester, silk, nylon, and aramid, and combinations thereof. The jacket surrounds a core made substantially or entirely of PBO. The core preferably includes three strands of PBO twisted at about three to six twists per inch.

The jacket most preferably comprises eight strands of PBO braided with six strands of polyester. Optionally, one or more tinted strands can be included in black or some other contrasting color as explained in greater detail below.

The suture of the present invention advantageously has the strength of Ethibond No. 5 suture, yet has the diameter, feel, and tie-ability of No. 2 suture. As a result, the suture of the present invention is ideal for most orthopedic procedures such as rotator cuff repair, Achilles tendon repair, patellar tendon repair, ACL/PCL reconstruction, hip and shoulder reconstruction procedures, and replacement for suture used in or with suture anchors.

The suture can be uncoated or coated. Typically useful coatings include wax (beeswax, petroleum wax, polyethylene wax, or others), silicone (Dow Corning silicone fluid 202A or others), silicone rubbers (Nusil Med 2245, Nusil Med 2174 with a bonding catalyst, or others), PTFE (Teflon, Hostaflon, or others), PBA (polybutylate acid), ethyl cellulose (Filodel), and others known in the art. The coatings improve lubricity of the braid, knot security, or abrasion resistance, for example.

Other features and advantages of the present invention will become apparent from the following description of the invention which refers to the accompanying drawings.

DETAILED DESCRIPTION OF THE INVENTION

Figure 1:
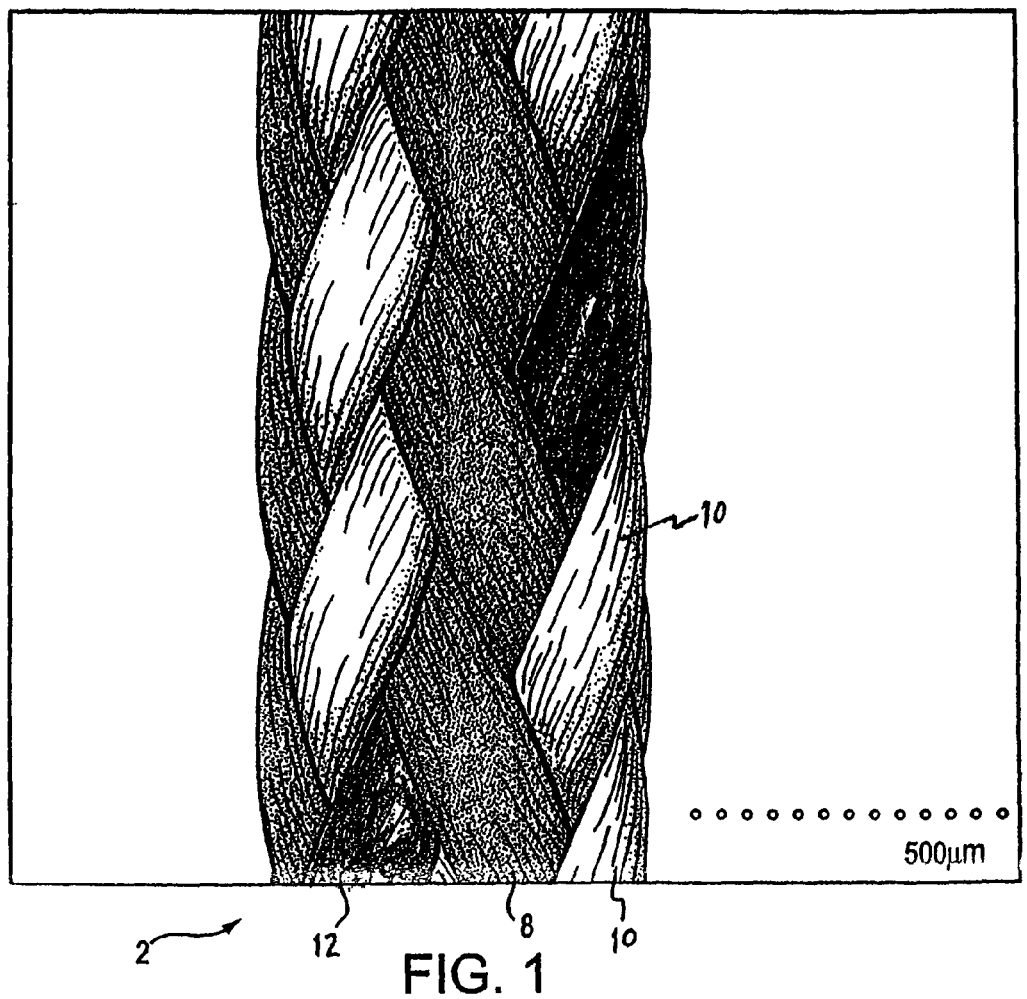
FIG. 1 is an enlarged detail view of a section of suture according to the present invention.
Figure 2:
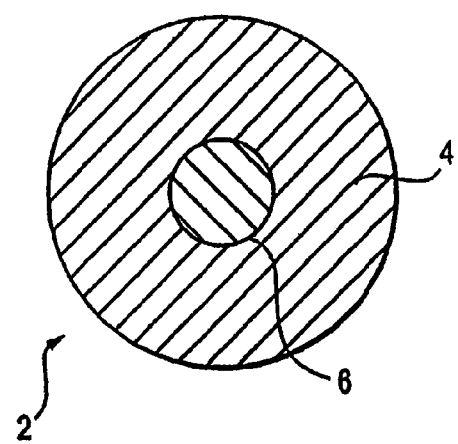
FIG. 2 is a schematic cross section of a length of suture according to the present invention.

Referring now to the drawings, where like elements are designated by like reference numerals, FIGS. 1 and 2 illustrate a section of suture 2 according to the present invention shown enlarged several fold. As illustrated in FIG. 2, suture 2 is made up of a jacket 4 and a core 6 surrounded by the jacket 4. Strands of PBO 8, optional strands of polyester 10, and optional colored strands 12 are braided together to form the jacket 4. Core 6 is formed of twisted strands of PBO.

Properties of PBO are included in the following Table:

| Type | | Regular AS | High Modulus HM |
|---|---|---|---|
| Filament decitex | Dtex | 1.7 | 1.7 |
| Density | g/cm³ | 1.54 | 1.56 |
| Moisture Regain (65% RH) | % | 2.0 | 0.6 |
| Tensile Strength | cN/dtex | 37 | 37 |
|  | GPa | 5.8 | 5.8 |
|  | KSI | 840 | 840 |
| Tensile Modulus | cN/dtex | 1150 | 1720 |
|  | GPa | 180 | 270 |
|  | MSI | 26 | 39 |
| Elongation at Break | % | 3.5 | 2.5 |
| Melting Temperature | ° C. | None | none |
| Decomposition Temperature in Air | ° C. | 650 | 650 |
| Coefficient of Thermal Expansion | ppm/° C. |  | −6 |
| Limiting Oxygen Index |  | 68 | 68 |
| Dielectric Constant at 100 kHz |  |  | 3.0 |
| Dissipation Factor |  |  | 0.001 |

In accordance with the present invention, optional colored traces 12 are preferably black. The black trace assists surgeons in distinguishing between suture lengths with the trace and suture lengths without the trace. Traces also assist the surgeon in identifying whether or not, and in what direction, the suture is moving. The trace can extend the entire length of the suture or only on half of a length of suture, the other half of the suture length remaining plain (white). Alternatively, the traces can form visibly distinct coding patterns on each half of the suture length. As a result, when the suture is threaded through the eyelet of a suture anchor, for example, the two legs (halves) of the length of suture are easily distinguished, and their direction of travel will be readily evident when the suture is pulled during surgery. Other patterns and arrangements of tracings also can be provided.

Details of the present invention will be described further below in connection with the following examples:

EXAMPLE 1

USP Size 5 (EP size 7)

Made on a 16 carrier Hobourns machine, the yarns used in the hollow, plain braided jacket are PBO, polyester type 712, and nylon. The jacket is formed using eight strands of PBO per carrier, braided with six strands of 100 decitex polyester, and two strands of tinted nylon. The core is formed of three carriers of PBO braided at three to six twists per inch. A No. 5 suture is produced.

EXAMPLE 2

Silk—Size 1

| Core: | 1 end of 144 dtex PBO × 3 |
|---|---|
| Jacket: | 5 carriers 95 dtex polyester |
|  | 6 carriers 144 dtex PBO |
|  | 1 carrier 84 dtex silk |

EXAMPLE 3

Silk—Size 2

| Core: | 1 end of 144 dtex PBO × 3 |
|---|---|
| Jacket: | 5 carriers 95 dtex polyester |
|  | 8 carriers 144 dtex PBO |
|  | 1 carrier 84 dtex silk |

To make various sizes of the inventive suture, different decitex values and different PPI settings can be used to achieve the required size and strength needed. In addition, smaller sizes may require manufacture on 12 carrier machines, for example. The very smallest sizes can be made without a core. Overall, the suture may range from 5% to 90% PBO (preferably at least 40% of the fibers are PBO), with the balance formed of enhancement strands, such as polyester and/or silk. The core preferably comprises 18% or greater of the total amount of filament.

The suture preferably is coated with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the braid, knot security, or abrasion resistance, for example.

The PBO component of the present invention provides strength, and the enhancement fiber (e.g., polyester) is provided to improve tie ability and tie down characteristics.

According to an alternative embodiment of the present invention, a partially bioabsorbable suture is provided by blending PBO fibers with a bioabsorbable material, such as PLLA or one of the other polylactides, for example. A suture made with about 10% PBO blended with absorbable fibers would provide greater strength than existing bioabsorbable suture, and with less stretch. Over time, 90% or more of the suture would absorb, leaving only a very small remnant of the knot. The absorbable suture can include coatings and tinted traces as noted above for nonabsorbable suture.

Figure 3:
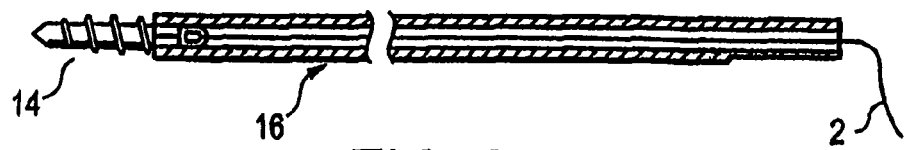
FIG. 3 is an illustration of the suture of the present invention attached to a suture anchor loaded onto a driver.
Figure 4A:
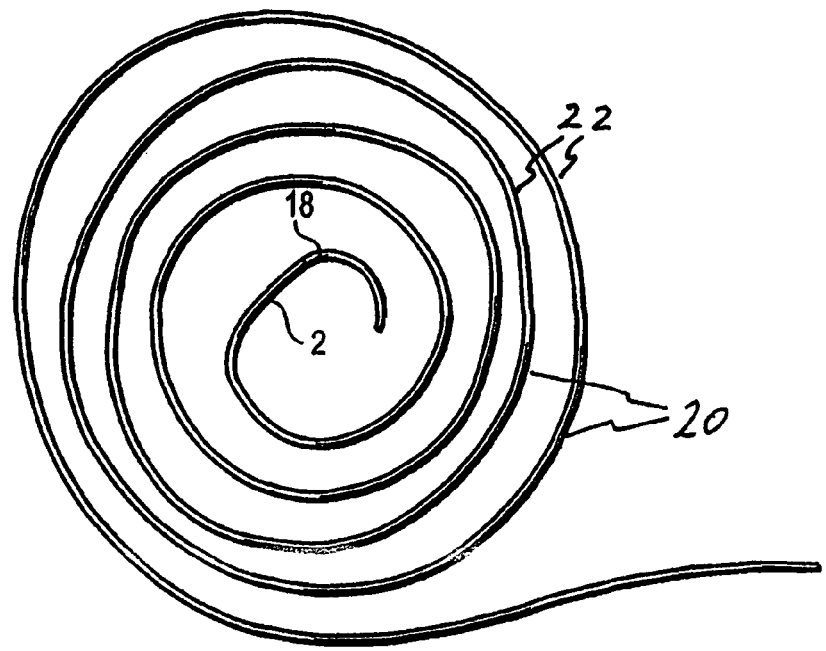
FIGS. 4A and 4B show the suture of the present invention attached to a half round, tapered needle.
Figure 4B:
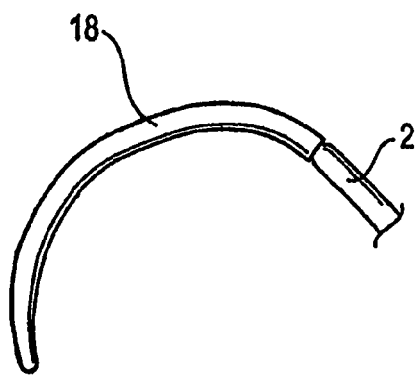

In one method of using the suture of the present invention, the suture 2 is attached to a suture anchor 14 as shown in FIG. 3 (prepackaged sterile with an inserter 16), or is attached at one or both ends to a half round, tapered needle 18 as shown in FIGS. 4A and 4B. FIG. 4A also illustrates a length of suture having regularly repeating pattern of trace threads according to the present invention. Sections 20 of the length of suture 2 have tinted tracing threads woven in, while sections 22 of the length of suture are plain, or otherwise are distinguishable from sections 20. The alternating patterned and plain sections aid the surgeon in determining the direction of suture travel when pulling the suture through tissue as viewed through an arthroscope, for example.

Figure 6:
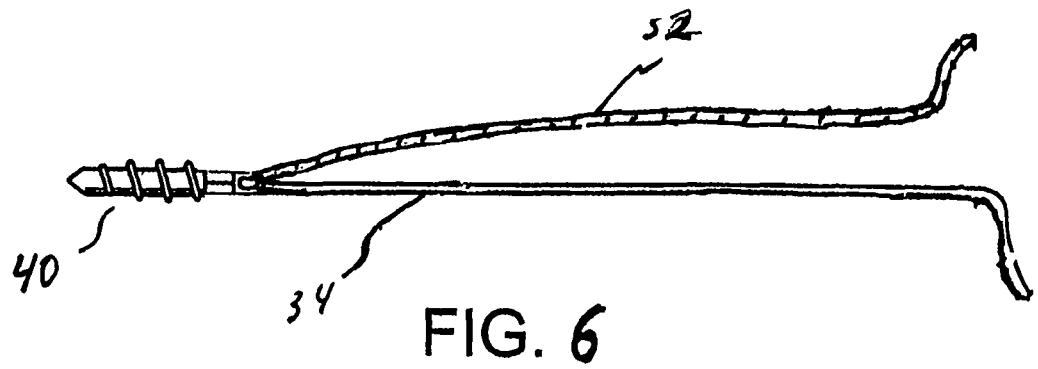
FIG. 6 illustrates a strand of suture according to the present invention provided on a suture anchor.
Figure 5:
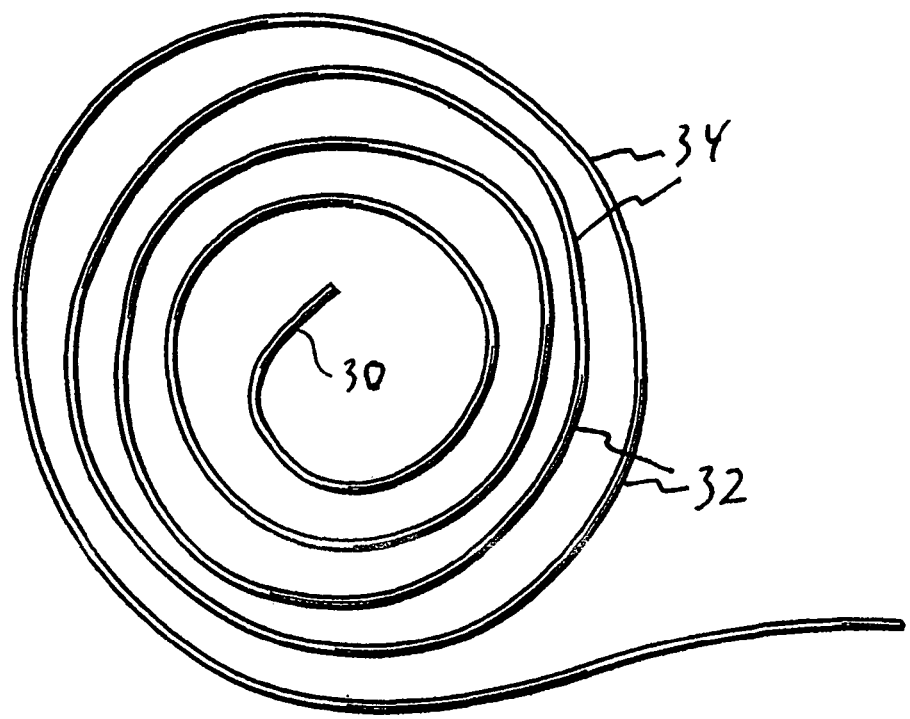
FIG. 5 illustrates a bulk length of suture of the present invention.

As shown in FIG. 5, to make the suture which has a trace only at one end, bulk suture 30 is provided with repeating sections 32 having trace threads separated by sections 34 having no trace threads. The bulk suture is cut between every other section, at one end of each plain section, for example, to provide lengths of suture that are half traced and half plain. Alternatively, the bulk suture can be cut midway through each section to provide a shorter suture having a trace at one end. The half-and-half lengths of suture can be threaded through the eyelet of a suture anchor 40, as shown in FIG. 6. As a further alternative, uniform lengths of the braided suture can be exposed, partially or completely, to the dye (dipped, sprayed, etc.) to provide suture lengths with partial or complete dying patterns. Accordingly, the identity of each leg of the suture strand provided on the suture anchor is easily decoded by a surgeon operating with the suture anchor assembly.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A braided suture suitable for use as a suture or ligature comprising fibers formed from filaments of poly(p-phenylene-2,6-benzobisoxazole) (PBO).

2. The braided suture of claim 1, further comprising at least one enhancement strand.

3. The braided suture of claim 2, wherein the enhancement strand is selected from the group consisting of polyester, silk, nylon, and aramid.

4. The braided suture of claim 2, wherein the at least one enhancement fiber comprises polyester strands.

5. The braided suture of claim 1, wherein the braid is hollow.

6. The braided suture of claim 5, further comprising a core formed within the hollow braid.

7. The braided suture of claim 6, wherein the core comprises fibers formed from PBO filaments.

8. The braided suture of claim 6, wherein the core comprises twisted fibers.

9. The braided suture of claim 1, further comprising a synthetic or natural fiber other than PBO blended with the braided fibers of PBO.

10. The braided suture of claim 9, comprising a plurality of fibers of at least one long chain synthetic polymer or bioabsorbable fiber braided with the PBO.

11. The braided suture of claim 9, wherein the long chain synthetic polymer is polyester, nylon, or both.

12. The braided suture of claim 9, wherein PBO fibers comprise at least 40% of the braided fibers.

13. The braided suture of claim 9, wherein polyester fibers comprise less than about 40% of the braided filaments.

14. A suture assembly comprising:
a suture formed of a plurality of braided fibers of poly(p-phenylene-2,6-benzobisoxazole) (PBO); and
a suture anchor attached to the suture.

15. The suture assembly as recited in claim 14, further comprising polyester fibers.

16. A suture assembly comprising:
a suture formed of a plurality of braided fibers of poly(p-phenylene-2,6-benzobisoxazole) (PBO); and
a half round, tapered needle attached to one or both ends of the suture.

17. A suture strand suitable for use as a suture or ligature including an outer jacket comprising a plurality of braided fibers of poly(p-phenylene-2,6-benzobisoxazole) (PBO).

* * * * *